(12) United States Patent
Netherton

(10) Patent No.: US 9,415,204 B2
(45) Date of Patent: Aug. 16, 2016

(54) FOCAL TISSUE STIMULATOR

(71) Applicant: Brett Lane Netherton, Prosperity, SC (US)

(72) Inventor: Brett Lane Netherton, Prosperity, SC (US)

( * ) Notice: Subject to any disclaimer, the term of this patent is extended or adjusted under 35 U.S.C. 154(b) by 132 days.

(21) Appl. No.: 14/211,330

(22) Filed: Mar. 14, 2014

(65) Prior Publication Data

US 2014/0277327 A1    Sep. 18, 2014

Related U.S. Application Data

(60) Provisional application No. 61/793,569, filed on Mar. 15, 2013.

(51) Int. Cl.
*A61N 1/04*   (2006.01)

(52) U.S. Cl.
CPC ............ *A61N 1/0472* (2013.01); *A61N 1/0456* (2013.01)

(58) Field of Classification Search
CPC ........................... A61N 1/0472; A61N 1/0456
See application file for complete search history.

(56) References Cited

U.S. PATENT DOCUMENTS

2009/0275936 A1 *  11/2009  Muller .......................... 606/33

* cited by examiner

*Primary Examiner* — Rex R Holmes
(74) *Attorney, Agent, or Firm* — Womble Carlyle Sandridge & Rice LLP

(57) ABSTRACT

A focal tissue stimulator is provided that includes a pair of concentric conductors. The conductors may include an inner conductor, and an outer conductor that has an elliptical annular shape and surrounds the inner conductor. The outer conductor may have a minor axis and a mutually-perpendicular, major axis, with a first portion of the outer conductor proximate the minor axis being closer in proximity to the inner conductor than a second portion of the outer conductor proximate the major axis. In this regard, the inner and outer conductors may be coupled or couplable to respective leads configured to deliver current for passage therebetween, with the elliptical annular shape of the outer conductor creating a pathway of increased current density at the first portion relative to the second portion.

9 Claims, 15 Drawing Sheets

FOCAL TISSUE STIMULATOR

CROSS-REFERENCE TO RELATED APPLICATION(S)

The present application claims priority to U.S. Provisional Patent Application No. 61/793,569, entitled: Focal Tissue Stimulator, filed on Mar. 15, 2013, the content of which is hereby incorporated by reference in its entirety.

TECHNOLOGICAL FIELD

The present disclosure relates generally to electrical stimulation of physiologic tissue and, in particular, to a focal tissue stimulator shaped to concentrate or focus stimulation current toward targeted physiologic tissue.

BACKGROUND

Electrical stimulation of physiologic tissue is common in medical practice. In particular, neural stimulation is a strong component of neurology/neurodiagnostics. This stimulation may be accomplished from skin surface stimulation, commonly called cutaneous stimulation or from direct nerve stimulation on exposed neural tissue when direct access to the nerve or brain tissue is available as is sometimes the case in surgery. The technique of electrically stimulating tissue is not without challenges. Two such challenges are electrical stimulus artifact and patient pain.

Electrical stimulus artifact occurs when current from the electrical stimulation electrode attachments flows in undesirable directions through tissue. For example, during stimulation of a nerve axon for purposes of depolarizing the nerve, the desired path for electrical current to flow would be from the attachment electrode cathode into tissue, through the desired nerve and back to the attachment electrode anode. In the ideal world, 100 percent of the delivered stimulating current would flow in this path without any current following alternate, undesirable pathways. However, in the real word, such ideal conditions do not occur and the delivered stimulating current flows in alternative, undesirable paths from anode to cathode in addition to the desired path through the targeted neural tissue. When these alternative, undesirable current pathways intersect with electrical recording activity, the result is the phenomena known as electrical stimulus artifact.

Electrical tissue stimulation can cause significant discomfort in the conscious patient. The pain results from the stimulation current activating tissue pain receptors. In order to minimize patient pain, it is desirable to activate the targeted neural (or other) tissue with the smallest possible delivered current while still facilitating the desired result in the targeted neural activation.

BRIEF SUMMARY

Example implementations of the present disclosure provide a focal tissue stimulator shaped to concentrate or focus stimulation current toward targeted physiologic tissue. Multiple techniques may be used to make this happen, including the use of geometric points and ovals or ellipses. Typically, in stimulating human tissue, an electrode pair is used (an electrode at times referred to herein as a conductor), typically referred to as anode and cathode. The use of geometric points placed in strategic locations may shift current density from the electrode in a specific direction. Likewise, the strategic use of oval or elliptical shapes may facilitate current density patterns. In some instances, tri-polar stimulation may be used, in which the same or a similar focusing mechanism may be achieved via geometric features.

According to one aspect of example implementations, a focal tissue stimulator is provided that includes a pair of concentric conductors. The conductors may include an inner conductor, and an outer conductor that has an elliptical annular shape and surrounds the inner conductor. The outer conductor may have a minor axis and a mutually-perpendicular, major axis, with a first portion of the outer conductor proximate the minor axis being closer in proximity to the inner conductor than a second portion of the outer conductor proximate the major axis. In this regard, the inner and outer conductors may be coupled or couplable to respective leads configured to deliver current for passage therebetween, with the elliptical annular shape of the outer conductor creating a pathway of increased current density at the first portion relative to the second portion.

In various examples, the conductors or certain parameters of the conductors may vary to optimize the current density of the pathway. In some examples, a distance of either or both of the minor axis or major axis may be selected to optimize the current density of the pathway.

In some examples, the inner conductor may include a (one or more) first pair of opposing, outwardly-extending pointed features that lie on an axis of the inner conductor coincident with the minor axis of the outer conductor. Similarly, the outer conductor may include a (one or more) second pair of facing, inwardly-extending pointed features that lie on the minor axis of the outer conductor. Here, the pointed features of the second pair of pointed features may face respective pointed features of the first pair of pointed features to focus the current density of the pathway.

In some further examples, the pointed features of the first pair of pointed features may be symmetric about the axis of the inner conductor coincident with the minor axis of the outer conductor, and the pointed features of the second pair of pointed features are symmetric about the minor axis of the outer conductor.

In some examples, the length and/or sharpness of the pointed features of either or both the first or second pair of pointed features may be selected to optimize the current density of the pathway.

In some examples, the inner conductor may include a plurality of first pairs of opposing, outwardly-extending pointed features the plurality of which lie on the axis of the inner conductor coincident with the minor axis of the outer conductor. Similarly, the outer conductor may include a plurality of second pairs of facing, inwardly-extending pointed features the plurality of which lie on the minor axis of the outer conductor. In these examples, the pointed features of the second pairs of pointed features may face respective pointed features of the first pairs of pointed features to focus the current density of the pathway.

In some examples, the distance between adjacent pointed features of either or both the first or second pairs of pointed features may be selected to optimize the current density of the pathway. In some examples, the orientation of adjacent pointed features of either or both the first or second pairs of pointed features may be selected to optimize the current density of the pathway.

In some examples, the plurality of first pairs of pointed features may be symmetric about the axis of the inner conductor coincident with the minor axis of the outer conductor, and the plurality of second pairs of pointed features may be symmetric about the minor axis of the outer conductor.

According to another aspect of example implementations, a focal tissue stimulator is provided that includes a pair of concentric conductors. The concentric conductors may include an inner conductor, and an outer conductor surrounding the inner conductor, the inner and outer conductors having respective coincident axes. The inner conductor may include a first pair of opposing, outwardly-extending pointed features that lie on the axis of the inner conductor, and the outer conductor may include a second pair of facing, inwardly-extending pointed features that lie on the axis of the outer conductor and face respective pointed features of the first pair of pointed features. The inner and outer conductors may be coupled or couplable to respective leads configured to deliver current for passage therebetween, with the pointed features of the inner and outer conductors creating a pathway of increased current density relative to the first and second conductors absent the pointed features.

In various examples, the conductors or certain parameters of the conductors may vary to optimize the current density of the pathway, such as in a manner similar to that described above and in greater detail below.

According to another aspect of example implementations, a focal tissue stimulator is provided that includes a pair of conductors. The conductors may include a first conductor, and a second conductor separate from the first conductor. The first and second conductors may have respective first axes and mutually-perpendicular second axes. The first axis of the second conductor may be separate from but parallel to the first axis of the first conductor, while the second axis of the second conductor may be coincident with the second axis of first conductor. The first conductor may include an outwardly-extending pointed feature that lies on the second axis of the first conductor and faces the second conductor. And the first and second conductors may be coupled or couplable to respective leads configured to deliver current for passage therebetween, with the pointed feature of the first conductor creating a pathway of increased current density relative to the first conductor absent the pointed feature.

In various examples, the conductors or certain parameters of the conductors may vary to optimize the current density of the pathway, such as in a manner similar to that described above and in greater detail below.

According to another aspect of example implementations, a focal tissue stimulator is provided that includes three conductors. The conductors may include a first conductor, a second conductor separate from the first conductor, and a third conductor separate from the first and second conductors. The first, second and third conductors may have respective first axes and mutually-perpendicular second axes, with the first axis of the first, second and third conductors being separate from but parallel to one another, and the second axis of the first, second and third conductors being coincident with one another. The first and third conductors may include respective outwardly-extending pointed features that lie on the second axis of respective ones of the first and third conductors, and that face the second conductor. And the second conductor may include a pair of opposing, outwardly-extending pointed features that lie on the second axis of the second conductor, the pointed features of the pair facing respective ones of the first and third conductors.

The first, second and third conductors may be coupled or couplable to respective leads configured to deliver current for passage between the first and second conductors, and between the second and third conductors. The pointed features of the first, second and third conductors, then, may create pathways of increased current density relative to the first, second and third conductors absent the pointed features.

Similar to before, in various examples, the conductors or certain parameters of the conductors may vary to optimize the current density of the pathway, such as in a manner similar to that described above and in greater detail below.

According to another aspect of example implementations, a focal tissue stimulator is provided that includes a plurality of conductors arranged in a grid including a plurality of rows and columns. According to this aspect, the conductors may have respective first axes and mutually-perpendicular second axes. The first axes of the conductors in any row of the grid and second axes of the conductors in any column of the grid may be separate from but parallel to one another, and the second axes of the conductors in any row of the grid and first axes of the conductors in any column of the grid may be coincident with one another.

The conductors may include respective outwardly-extending pointed features that lie on either or both of the respective first or second axes, and that face adjacent conductors in the grid. In this regard, the conductors may be coupled or couplable to respective leads configured to deliver current for passage therebetween, with the pointed features of the conductors creating pathways of increased current density relative to the conductors absent the pointed features.

According to yet another aspect of example implementations, a focal tissue stimulator is provided that includes one or more depth electrodes. Each depth electrode may include a first electrical contact, and a second electrical contact separate from the first electrical contact, with the first and second electrical contacts being positioned on the electrode along a length thereof. The first and second electrical contacts may include respective outwardly-extending pointed features that face one another. And the first and second electrical contacts may be coupled to the electrode configured to deliver current for passage therebetween, with the pointed features of the first and second electrical contacts creating a pathway of increased current density relative to the first and second electrical contacts absent the pointed feature.

BRIEF DESCRIPTION OF THE DRAWING(S)

Having thus described example implementations of the present disclosure in general terms, reference will now be made to the accompanying drawings, which are not necessarily drawn to scale, and wherein:

DETAILED DESCRIPTION

Figure 1:
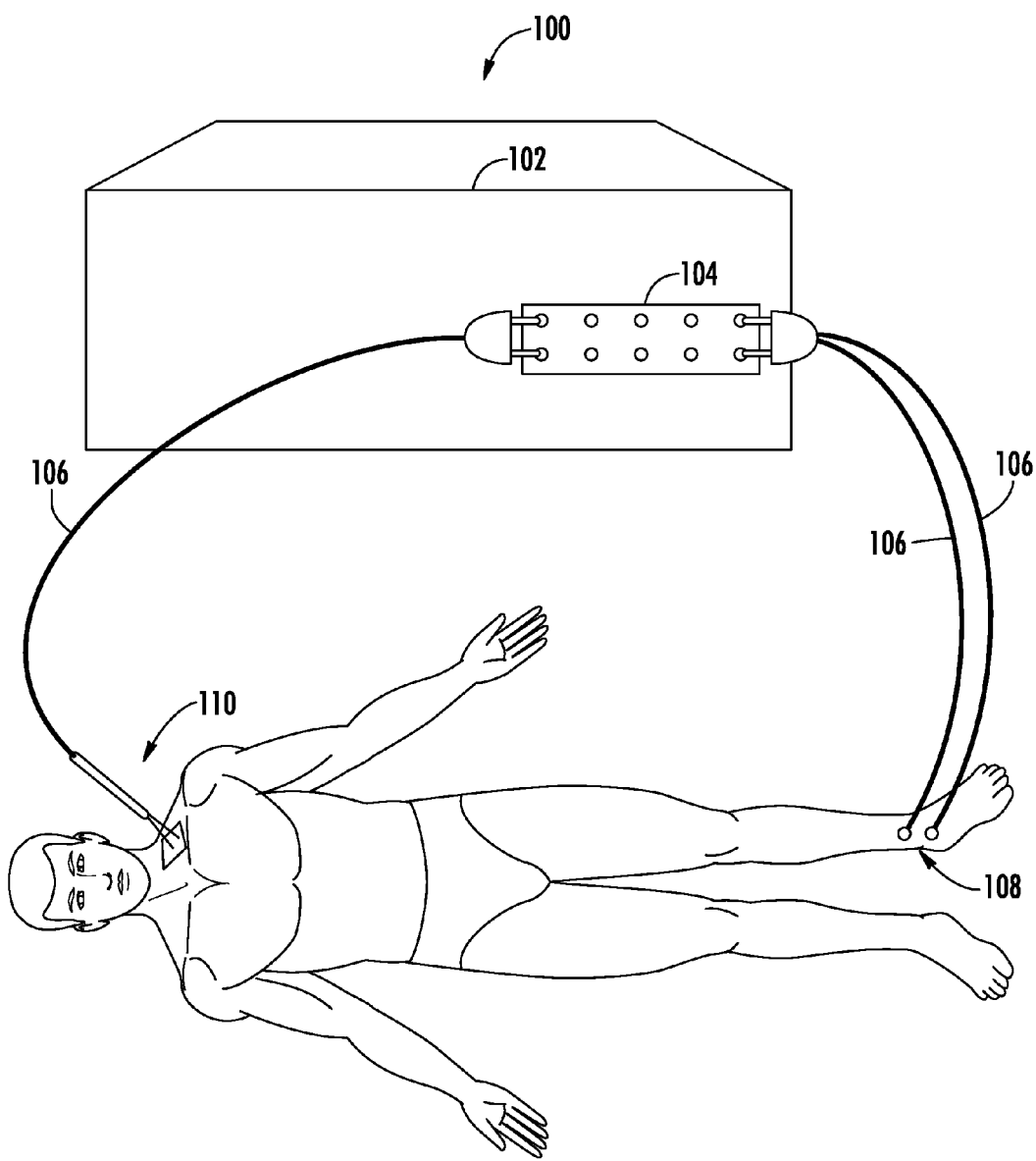
FIG. 1 is an illustration of a physiological tissue stimulation configuration, in accordance with an example implementation of the present disclosure.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. Like reference numerals refer to like elements throughout.

FIG. 1 is an illustration of a physiological tissue stimulation configuration 100, in accordance with an example implementation of the present disclosure. As shown, the configuration includes a neurodiagnostic machine 102 including a plurality of tissue/nerve stimulation outputs 104. These outputs may be connected by leads 106 to focal tissue stimulators that may be contacted with a patient. As shown in FIG. 1, there may be two different ways (both very common) that tissue may be stimulated, namely cutaneous stimulation and direct-nerve stimulation. In cutaneous stimulation, one can place, adhere or otherwise affix one type of focal tissue stimulator, namely surface (often called cutaneous) electrodes 108, on the skin and stimulate with enough current to go through the skin down to the desired nerve. In direct-nerve stimulation, when nerves are exposed, one can place another type of focal tissue stimulator, namely direct-nerve stimulators 110, in direct contact with them and stimulate. As one can imagine, lower current intensities are required to activate the nerve when using direct nerve stimulation. In addition, the patient is going to be under anesthesia when direct nerve stimulation techniques are used. And in addition, the direct nerve stimulation is going to be used in a wound when the skin has been bypassed.

Figure 2:
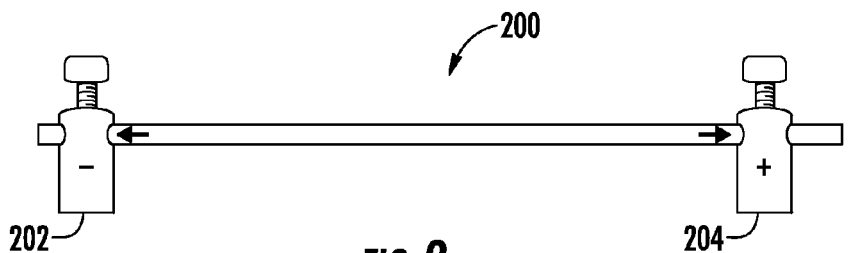
FIG. 2 is an illustration of an electrode pair including an anode and a cathode, in accordance with one example implementation.

FIG. 2 is an illustration of an electrode pair 200 including an anode 202 and a cathode 204, in accordance with one example implementation. As shown in FIG. 2, in an ultra-low impedance material such as a copper wire, one may have a very clear current pathway from cathode to anode along the wire, as long at the wire is in parallel with a high impedance alternative pathway such as air. This situation is in great contrast to stimulating tissue with two different attached electrodes. Tissue does have considerable impedance gradients, but once the relatively high impedance of skin has been breached, the tissues underneath are relatively conductive. The result is that current density patterns are quite diverse. In short, current is going to spread out all over the place, unlike the situation with the copper wire.

Figure 3:
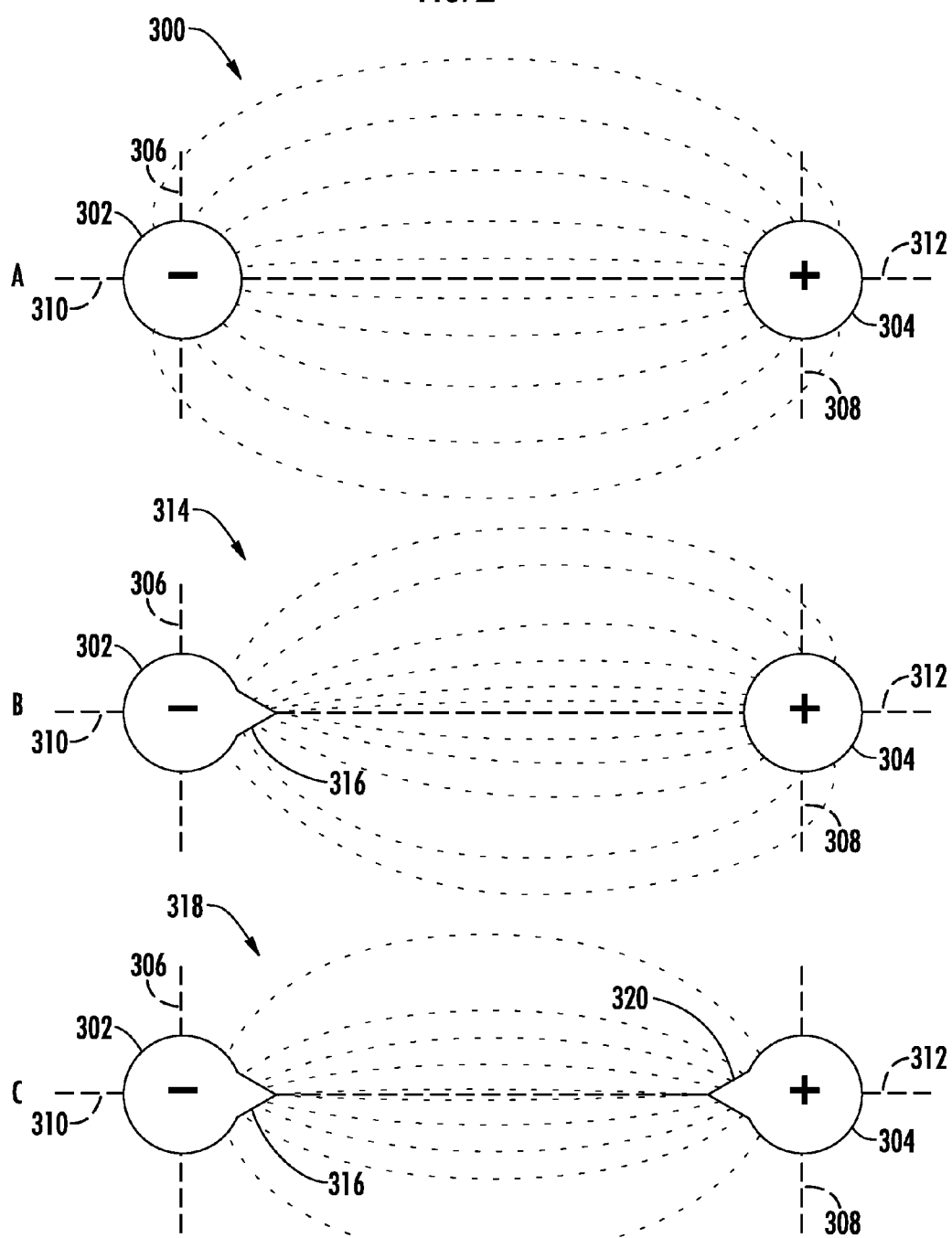
FIG. 3 (including A, B and C) is an illustration of electrode pairs of respective focal tissue stimulators, according to example implementations.

FIG. 3 (including A, B and C) is an illustration of electrode pairs of respective focal tissue stimulators, according to example implementations. As shown in FIG. 3(A), a focal tissue stimulator 300 is provided that includes a pair of conductors. The conductors may include a first conductor 302, and a second conductor 304 separate from the first conductor. The first and second conductors may have respective first axes 306, 308 and mutually-perpendicular second axes 310, 312. The first axis of the second conductor may be separate from but parallel to the first axis of the first conductor, while the second axis of the second conductor may be coincident with the second axis of first conductor.

FIG. 3(B) illustrates a focal tissue stimulator 314 according to some example implementations of the present disclosure, which may further include one or more features to concentrate current density between the conductors. In this regard, its first conductor 302 may include an outwardly-extending pointed feature 316 that lies on the second axis of the first conductor and faces the second conductor. In some examples, as shown in FIG. 3(C) a focal tissue stimulator 318 may include pointed features on both of its conductors. That is, the second conductor 304 may likewise include an outwardly-extending pointed feature 320 that lies on the second axis of the second conductor and faces the first conductor. The first and second conductors may be coupled or couplable to respective leads configured to deliver current for passage therebetween, with the pointed feature of the first conductor creating a pathway of increased current density relative to the first conductor absent the pointed feature. And in instances including the pointed feature of the second conductor, it may further increase the current density of the pathway In these examples, when the conductors 302, 304 (electrodes) are placed against tissue and electrically stimulated, the current density will tend to concentrate where there is a sharp point due to physics principles of charges concentrating on points such as those of the pointed features 316, 320. Being able to focus the current density between two conductors on tissue is very desirable. There are a number of benefits from being able to focus stimulation.

First, since the current is more focused on the target tissue, the clinician can deliver lower total current intensities while still delivering the same target tissue current density. In this case, the patient feels less pain upon stimulation. Second, focusing the current density means less current flowing in unwanted, alternate pathways. This inherently decreases the amount of current available to create electrical stimulus artifact. Third, the clinician will have a better knowledge of the current pathway and can place the conductors accordingly.

Figure 4:
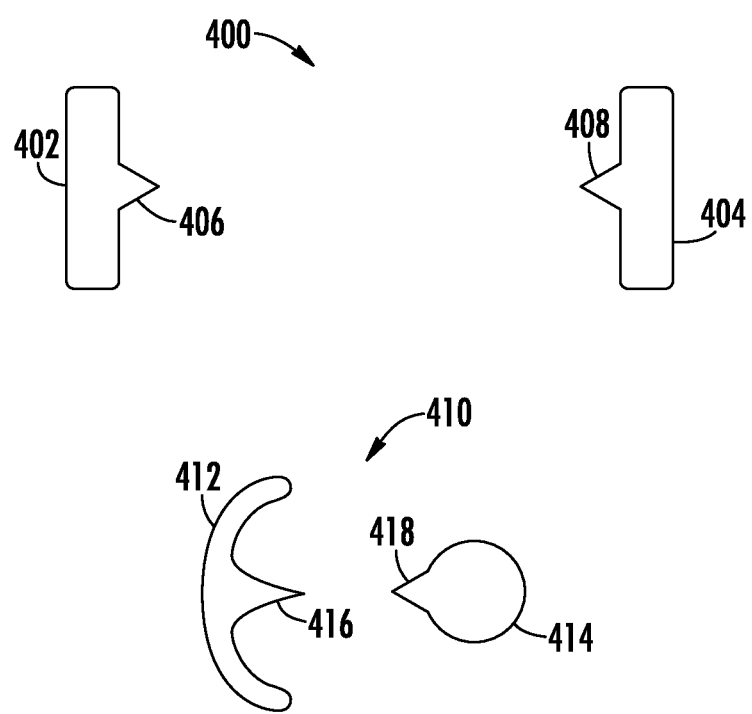
FIG. 4 and FIG. 5 (including A, B, C and D) are illustrations of electrode pairs of respective focal tissue stimulators, according to other example implementations.

In various examples, as explained in greater detail below in FIGS. 7 and 8 relative to other example implementations but equally applicable here, the conductors 302, 304, their pointed features 316, 320 or certain parameters of the conductors or their pointed features may vary to optimize the current density of the pathway. The focal tissue stimulator may also include conductors of varying shapes. FIG. 4 illustrates two such focal tissue stimulators. In one focal tissue stimulator 400, the conductors 402, 404 may be rectangular shaped and include respective pointed features 406, 408 facing one another. In another focal tissue stimulator 410, one of the conductors 412 may have a crescent shape while the other conductor 414 has a circular shape, and both may include respective pointed features 416, 418 facing one another.

Figure 5:
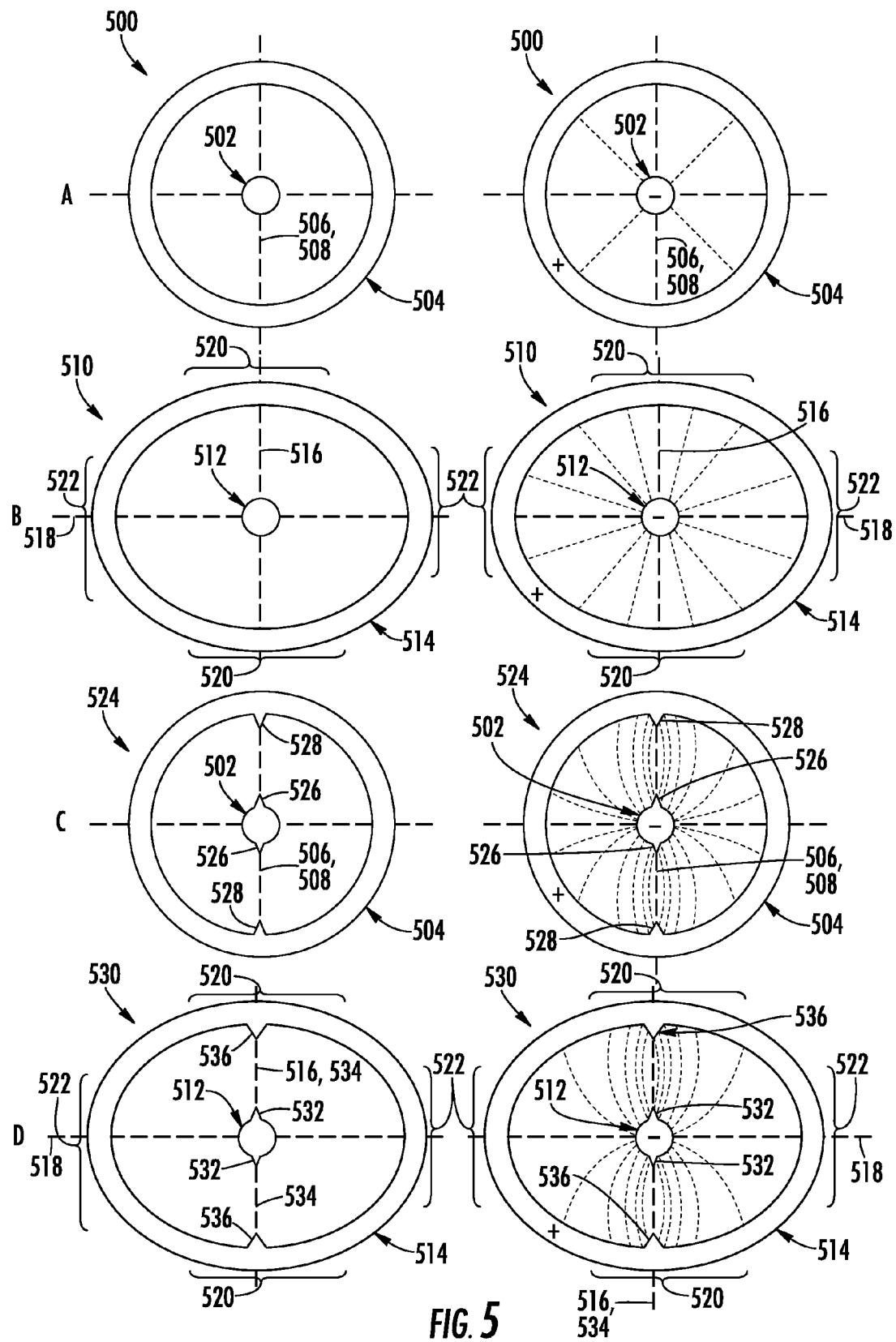

FIG. 5 (including A, B, C and D) are illustrations of electrode pairs of respective focal tissue stimulators, according to other example implementation. FIG. 5 illustrates four different focal tissue stimulators, each of the four in a pair of illustrations—namely with and without showing current density between the conductors (anode and cathode).

FIG. 5(A) illustrates a focal tissue stimulator 500 including includes a pair of concentric conductors (anode and cathode). The concentric conductors may include an inner conductor 502, and an outer conductor 504 surrounding the inner conductor, the inner and outer conductors having respective coincident axes 506, 508. The inner and outer conductors may be coupled or couplable to respective leads configured to deliver current for passage therebetween. Upon stimulation, the current density should be uniform around the conductors. It should be noted that using a concentric stimulating electrode dramatically decreases stimulus artifact in recordings compared to the use of two non-concentric conductors.

FIG. 5(B) illustrates another example a focal tissue stimulator 510 that includes a pair of concentric conductors. The conductors may include an inner conductor 512, and an outer conductor 514 that has an elliptical annular shape and surrounds the inner conductor. The outer conductor may have a minor axis 516 and a mutually-perpendicular, major axis 518, with a first portion 520 of the outer conductor proximate the minor axis being closer in proximity to the inner conductor than a second portion 522 of the outer conductor proximate the major axis. In this regard, the inner and outer conductors may be coupled or couplable to respective leads configured to deliver current for passage therebetween, with the elliptical annular shape of the outer conductor creating a pathway of increased current density at the first portion relative to the second portion. That is, upon stimulation, the current density should be higher at the points of closest proximity, creating some current density focus.

As shown in FIG. 5(C) relative to the aforementioned focal tissue stimulator 500, a similar focal tissue stimulator 524 may be provided in which the inner conductor 502 may include a (one or more) first pair of opposing, outwardly-extending pointed features 526 that lie on the axis 506 of the inner conductor, and the outer conductor 504 may include a (one or more) second pair of facing, inwardly-extending pointed features 528 that lie on the axis 508 of the outer conductor and face respective pointed features of the first pair of pointed features. Here, the pointed features of the inner and outer conductors may create a pathway of increased current density 528 relative to the first and second conductors absent the pointed features.

As shown in FIG. 5(D) relative to the focal tissue stimulator 510, another similar focal tissue stimulator 530 may likewise include pointed features. That is, the inner conductor 512 may include a (one or more) first pair of opposing, outwardly-extending pointed features 532 that lie on an axis 534 of the inner conductor coincident with the minor axis 516 of the outer conductor 514. Similarly, the outer conductor may include a (one or more) second pair of facing, inwardly-extending pointed features 536 that lie on the minor axis of the outer conductor. Here, the pointed features of the second pair of pointed features may face respective pointed features of the first pair of pointed features to focus the current density of the pathway. This design may elicit consistent evoked potentials with lower current intensities. And its use may decrease stimulus artifact and required delivered currents.

Figure 6:
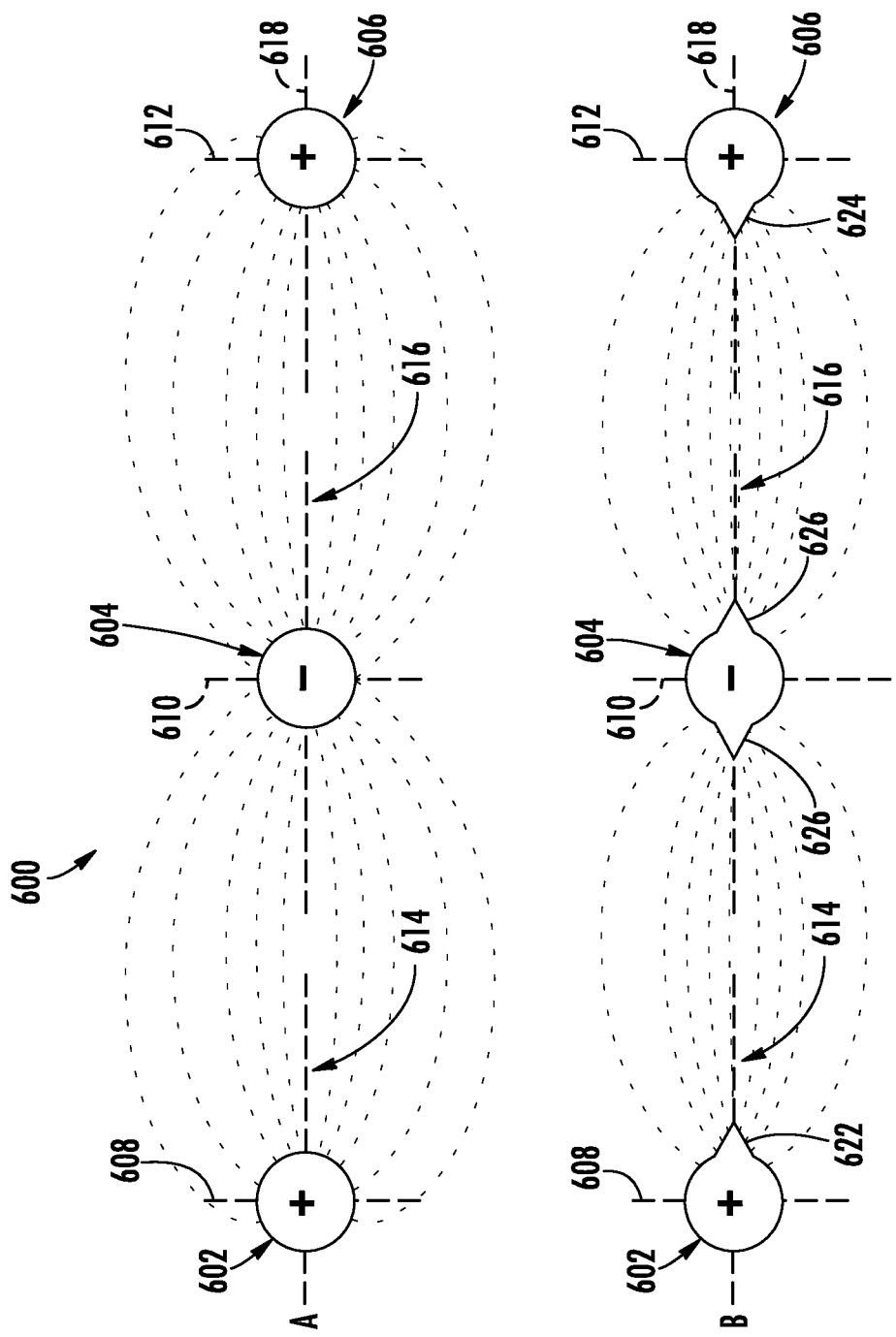
FIG. 6 (including A and B) is an illustration of electrode pairs of respective tri-polar focal tissue stimulators, according to example implementations.

FIG. 6 (including A and B) is an illustration of electrode pairs of respective tri-polar focal tissue stimulators, according to example implementation. As shown in FIG. 6(A), a focal tissue stimulator 600 is provided that includes three conductors. The conductors may include a first conductor 602, a second conductor 604 separate from the first conductor, and a third conductor separate 606 from the first and second conductors. The first, second and third conductors may have respective first axes 608, 610, 612 and mutually-perpendicular second axes 614, 616, 618, with the first axis of the first, second and third conductors being separate from but parallel to one another, and the second axis of the first, second and third conductors being coincident with one another.

As shown in FIG. 6(B), in a similar focal tissue stimulator 620, the first and third conductors may include respective outwardly-extending pointed features 622, 624 that lie on the second axis of respective ones of the first and third conductors, and that face the second conductor. And the second conductor may include a pair of opposing, outwardly-extending pointed features 626 that lie on the second axis of the second conductor, the pointed features of the pair facing respective ones of the first and third conductors.

The first, second and third conductors 602, 604, 606 may be coupled or couplable to respective leads configured to deliver current for passage between the first and second conductors, and between the second and third conductors. The pointed features 622, 624, 626 of the first, second and third conductors, then, may create pathways of increased current density relative to the first, second and third conductors absent the pointed features.

Similar to before, in various examples, the conductors 602, 604, 606, their pointed features 622, 624 or certain parameters of the conductors or their pointed features may vary to optimize the current density of the pathway, such as in a manner similar to that explained in greater detail below with reference to FIGS. 7 and 8.

Figure 7:
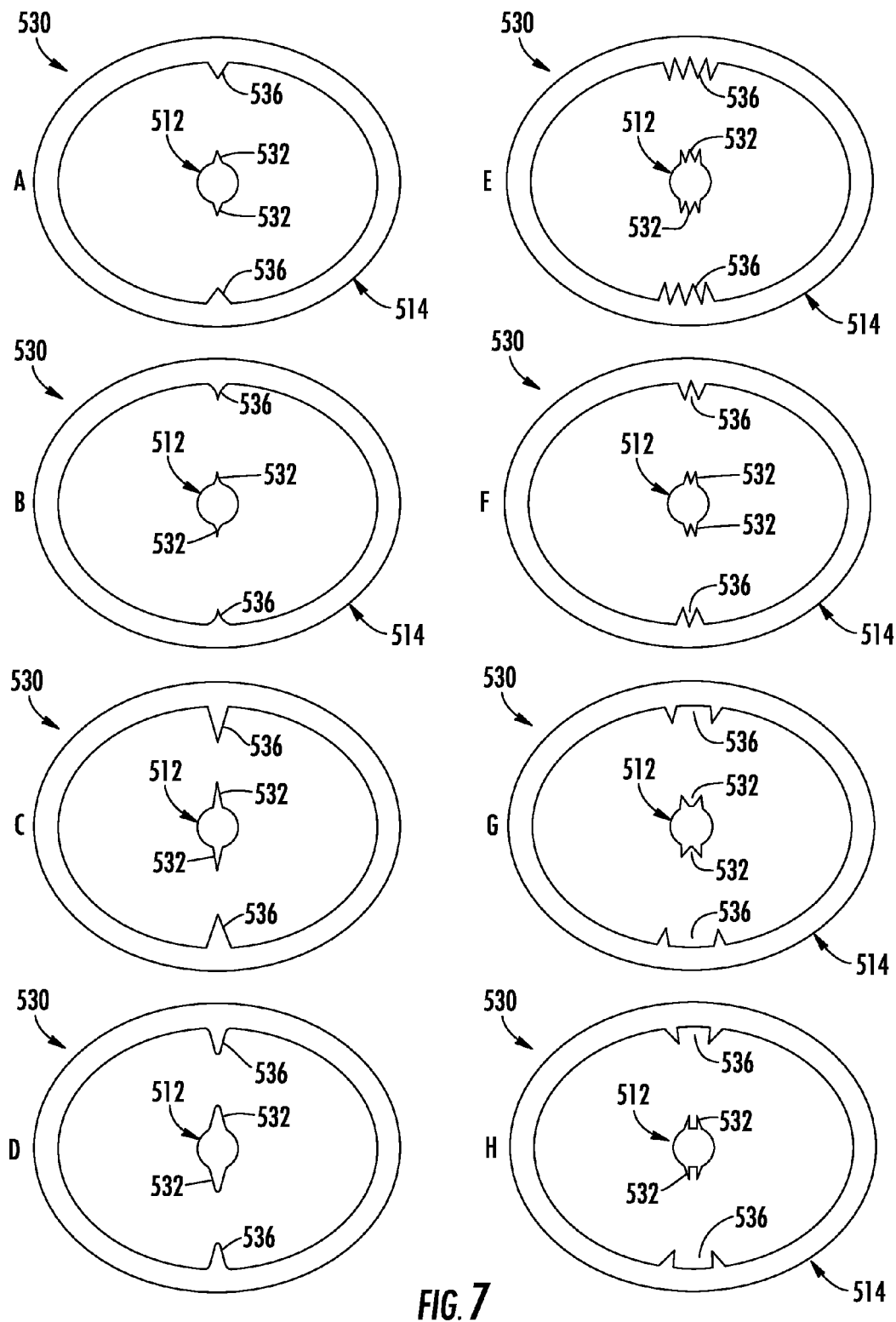
FIG. 7 illustrates a number of parameters that may vary for various electrode designs, according to example implementations.

Returning to the examples of FIG. 5 but now with reference to FIG. 7, in various examples, the conductors 502, 504, 512, 514, their pointed features 526, 528, 532, 536 or certain parameters of the conductors or their pointed features may vary to optimize the current density of the pathway. In some examples, the distance of either or both of the minor axis 516 or major axis 518 may be selected to optimize the current density of the pathway. FIG. 7 illustrates a number of other variations with respect to the example of FIG. 5(D), which is repeated in FIG. 7(A). FIGS. 7(B), 7(C) and 7(D) show example variations in which the thickness/width, length and/or sharpness of the pointed features 532, 536 of either or both the first or second pair of pointed features may be selected to optimize the current density of the pathway.

As shown in FIGS. 7(E), 7(F), 7(G) and 7(H), in some examples, the inner conductor 512 may include a plurality of first pairs of opposing, outwardly-extending pointed features 532 the plurality of which lie on the axis 534 of the inner conductor coincident with the minor axis 516 of the outer conductor 514. Similarly, the outer conductor may include a plurality of second pairs of facing, inwardly-extending pointed features 536 the plurality of which lie on the appropriate axis or minor axis of the outer conductor. In these examples, the pointed features of the second pairs of pointed features may face respective pointed features of the first pairs of pointed features to focus the current density of the pathway. And in some examples, as shown in particular in FIG. 7(G), the distance between adjacent pointed features of either or both the first or second pairs of pointed features may be selected to optimize the current density of the pathway.

In some further examples, the pointed features 532 of the first pair of pointed features may be symmetric about the axis 534 of the inner conductor 512, and the pointed features 536 of the second pair of pointed features are symmetric about the minor axis 516 of the outer conductor. Or in the case of multiple first and second pairs, the respective pluralities may be symmetric about the aforementioned axes. And in some examples, the orientation of adjacent pointed features of either or both the first or second pairs of pointed features may be selected to optimize the current density of the pathway, as shown in FIG. 7(H).

Figure 8:
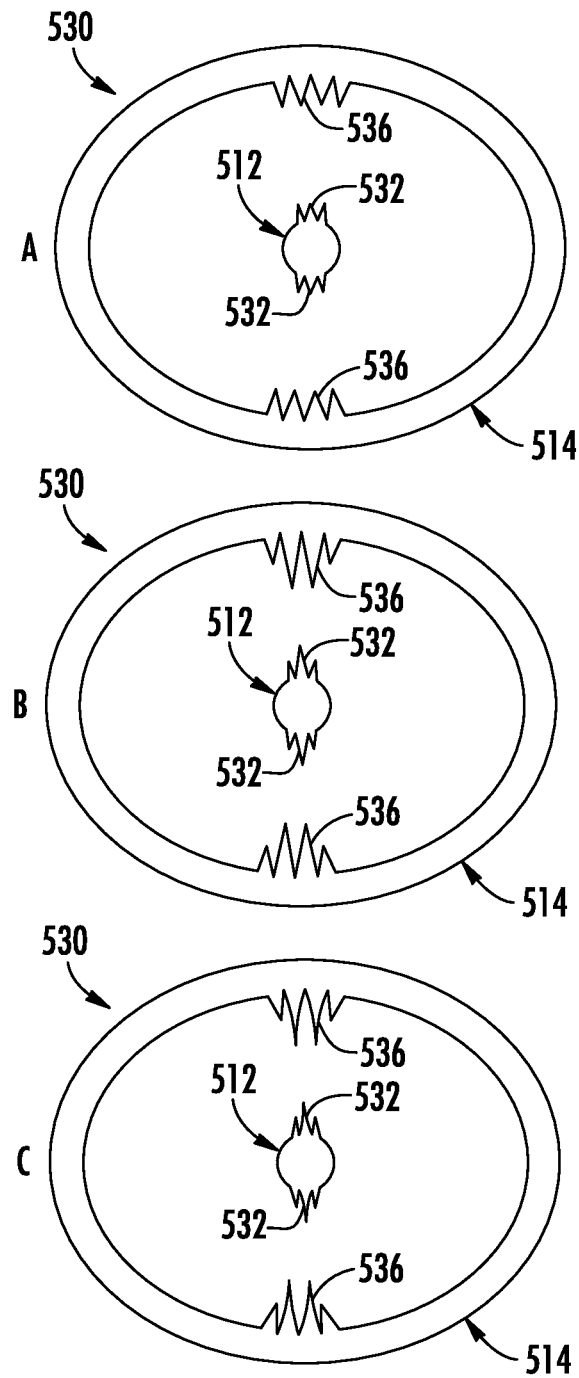
FIG. 8 illustrates a number of parameters that may vary for various electrode designs according to example implementations.

Like FIG. 7, FIG. 8 illustrates a number of parameters that may vary for variations of the focal tissue stimulator of example implementations, with reference again to the stimulator 530 of FIG. 5(D). FIG. 8(A) illustrates an example including multiple first and second pairs of pointed features 532, 536. FIG. 8(B), then, shows that the length of adjacent pointed features may be optimized at different lengths. And FIG. 8(C) shows that the combination of the lengths and orientation of the pointed features may be optimized.

Figure 9:
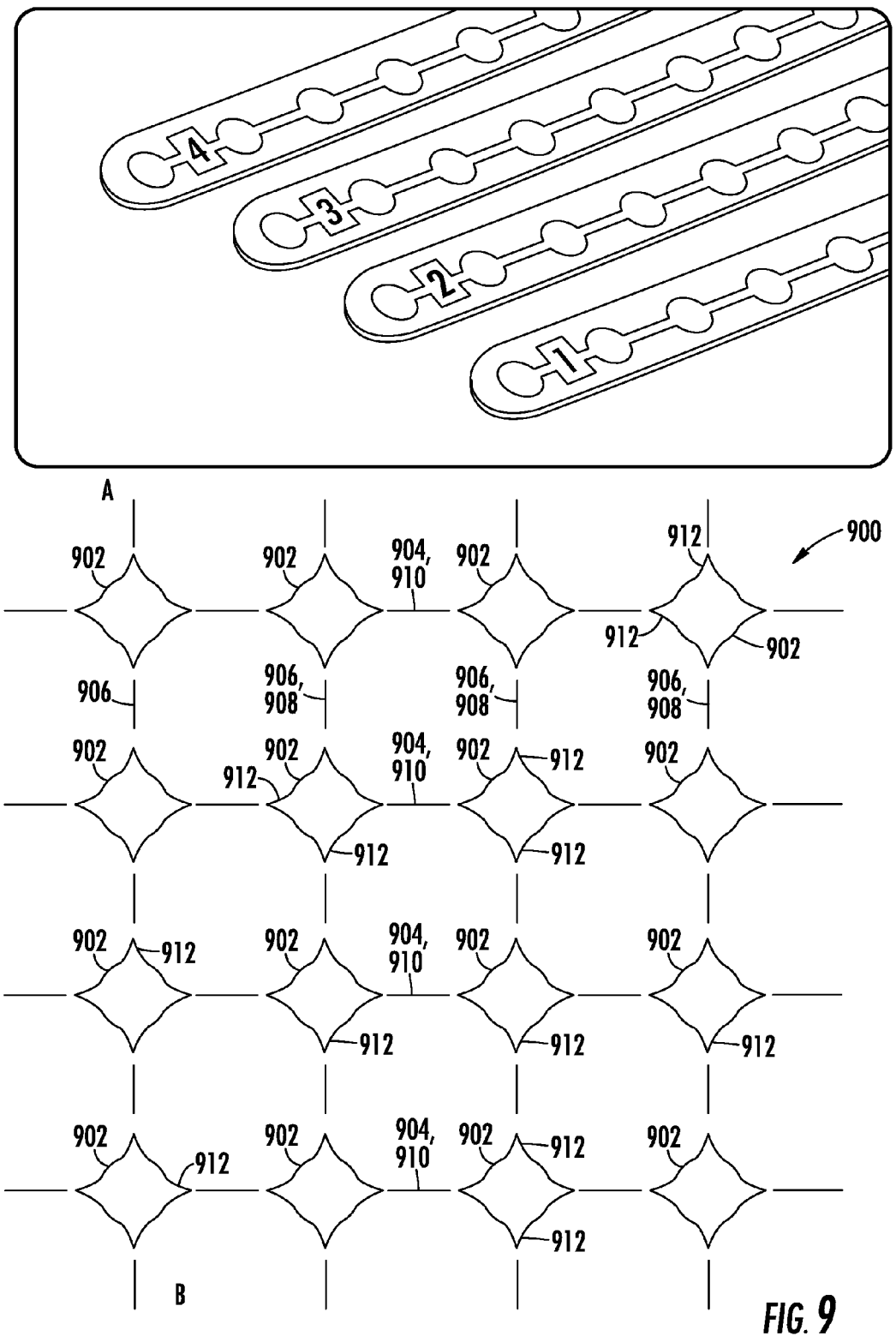
FIG. 9 illustrates (A) commercially-available grid electrodes, and (B) a focal tissue stimulator including grid electrodes according to example implementations of the present disclosure.

FIG. 9(A) illustrates grid electrodes that are commonly used in brain and spine surgery. These are frequently used for recording of neural activity. However, they can be used for tissue stimulation. FIG. 9(B) shows one example implementation of a focal tissue stimulator 900 that may facilitate lower stimulus intensities between two stimulation points.

As shown, the focal tissue stimulator 900 includes a plurality of conductors 902 arranged in a grid including a plurality of rows 904 and columns 906. According to this aspect, the conductors may have respective first axes 908 and mutually-perpendicular second axes 910. The first axes of the conductors in any row of the grid and second axes of the conductors in any column of the grid may be separate from but parallel to one another, and the second axes of the conductors in any row of the grid and first axes of the conductors in any column of the grid may be coincident with one another.

The conductors 902 may include respective outwardly-extending pointed features 912 (only some of which are separately called out) that lie on either or both of the respective first or second axes 908, 910, and that face adjacent conductors in the grid of rows 904 and columns 906. In this regard, the conductors may be coupled or couplable to respective leads configured to deliver current for passage therebetween, with the pointed features of the conductors creating pathways of increased current density relative to the conductors absent the pointed features.

Similar to before, in various examples, the conductors 902, their pointed features 912 or certain parameters of the conductors or their pointed features may vary to optimize the current density of the pathway, such as in a manner similar to that described above with reference to FIGS. 7 and 8.

Figure 10:
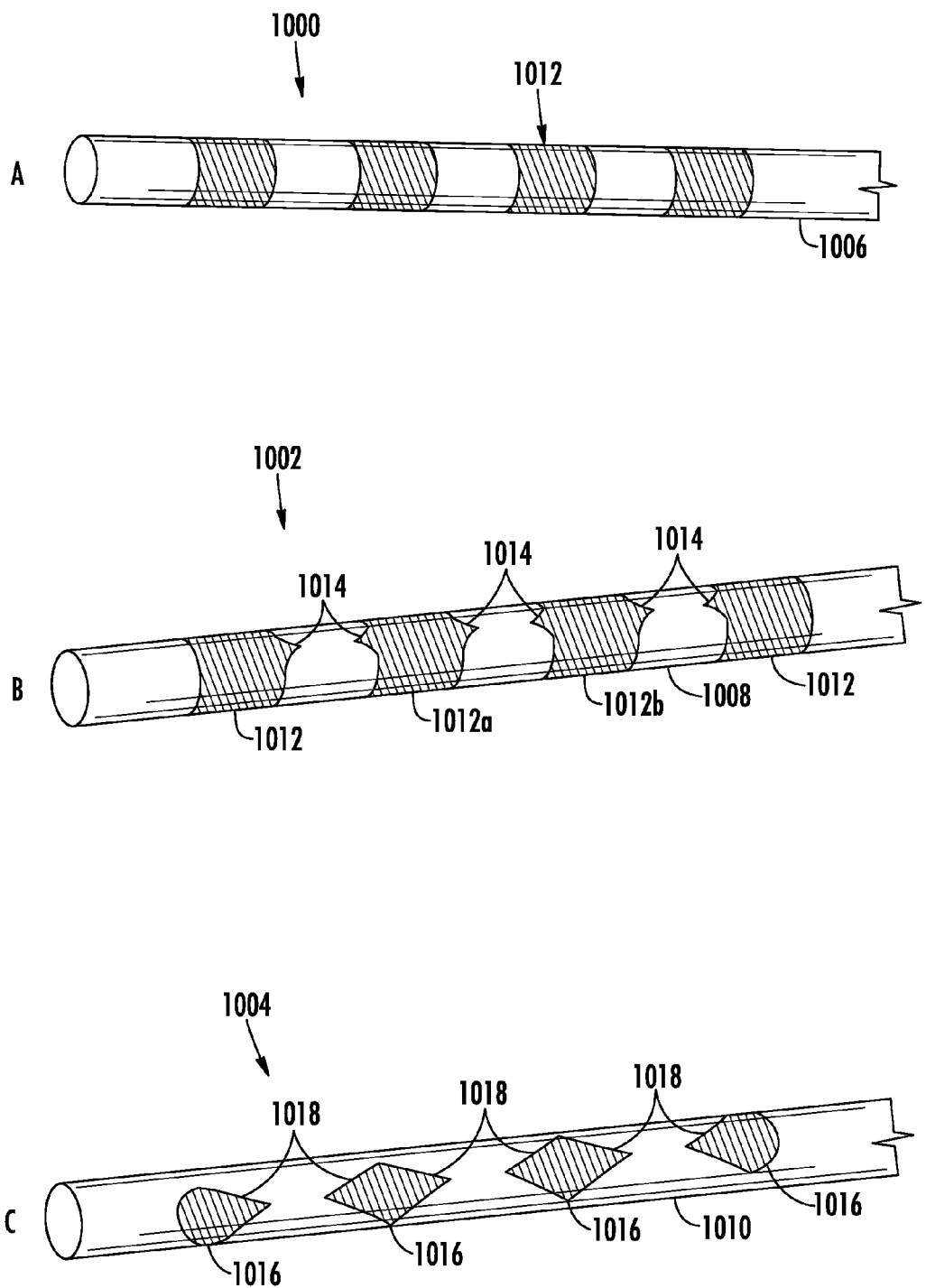
FIG. 10 (including A, B and C) illustrates depth electrodes according to example implementations.

Reference is now made to FIG. 10 (including A, B and C), which illustrate focal tissue stimulators 1000, 1002, 1004 including one or more depth electrodes 1006, 1008, 1010 according to example implementations. In some examples, depth electrodes such as these may be used for deep brain stimulation are thin, and may be round slightly flexible electrodes with multiple electrical contacts. These contacts may be circumferentially oriented contacts 1012 around the electrode as in FIG. 10(A), and which may include pointed features 1014 as in FIG. 10(B) and described below. And FIG. 10(C) illustrates a similar focal tissue stimulator with electrical contacts 1016 in a non-circumferential orientation with pointed features 1018. Note that others of the example shapes could be included in a depth electrode.

In the example of FIG. 10(B)—and similarly FIG. 10(C), each depth electrode 1012 may include a first electrical contact 1012*a*, and a second electrical contact 1012*b* separate from the first electrical contact, with the first and second electrical contacts being positioned on the electrode along a length thereof. The first and second electrical contacts may include respective outwardly-extending pointed features 1014 that face one another. And the first and second electrical contacts may be coupled to the electrode configured to deliver current for passage therebetween, with the pointed features of the first and second electrical contacts creating a pathway of increased current density relative to the first and second electrical contacts absent the pointed feature.

Similar to before, in various examples, the electrical contacts 1014, 1018, their pointed features 1014, 1018 or certain parameters of the electrical contacts or their pointed features may vary to optimize the current density of the pathway, such as in a manner similar to that described above with reference to FIGS. 7 and 8.

Figure 11:
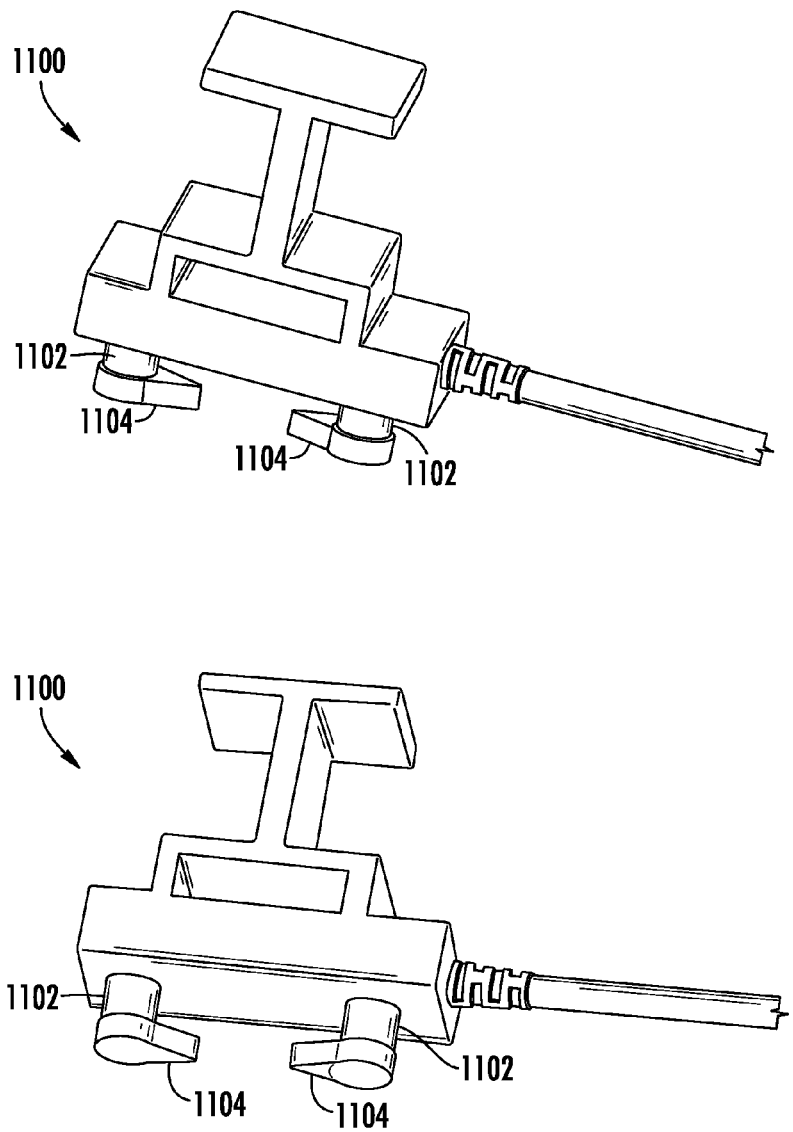
FIG. 11 illustrates handheld bar electrodes according to example implementations.
Figure 12:
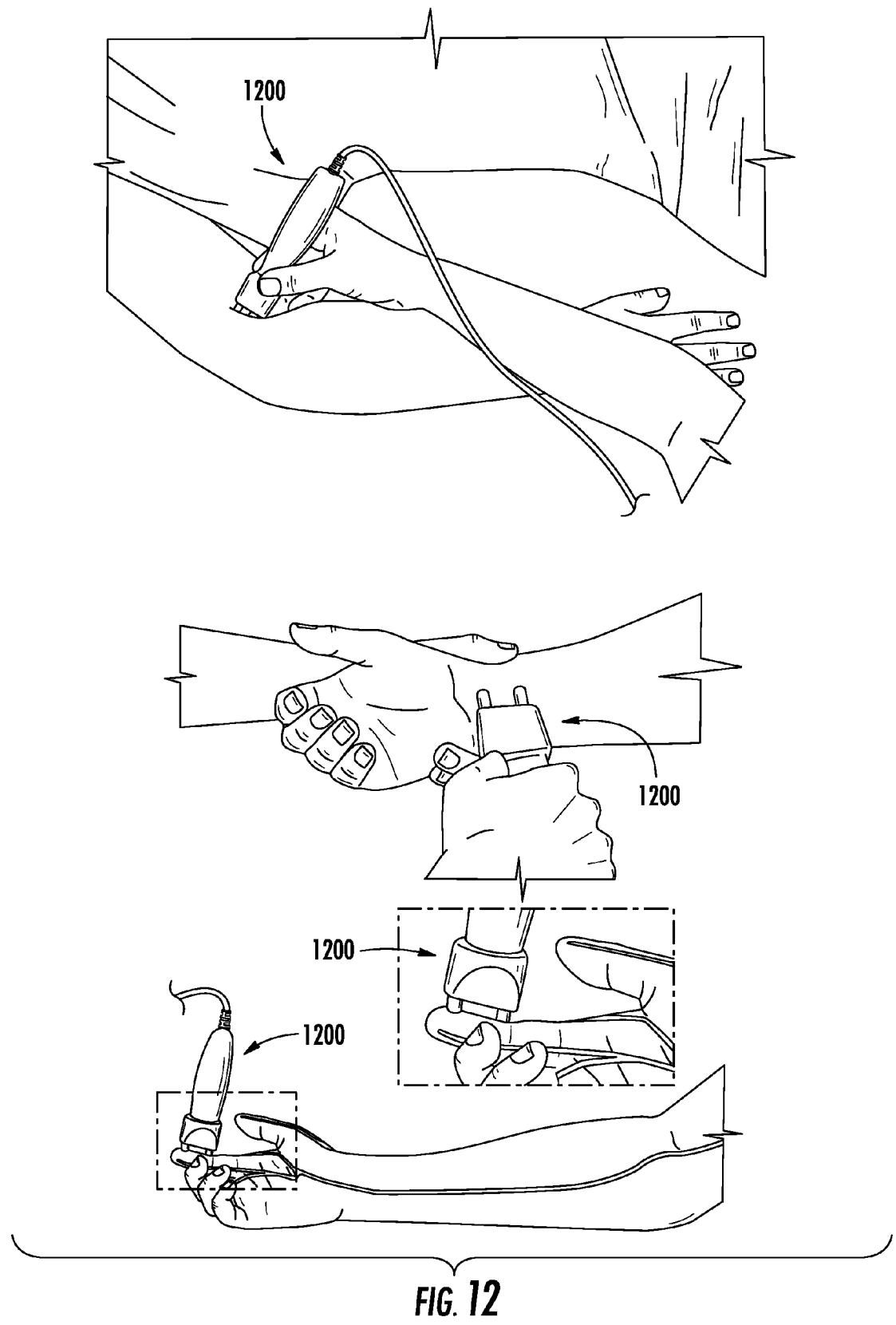
FIG. 12 illustrates a handheld nerve conduction stimulator that may benefit from example implementations of the present disclosure.
Figure 13:
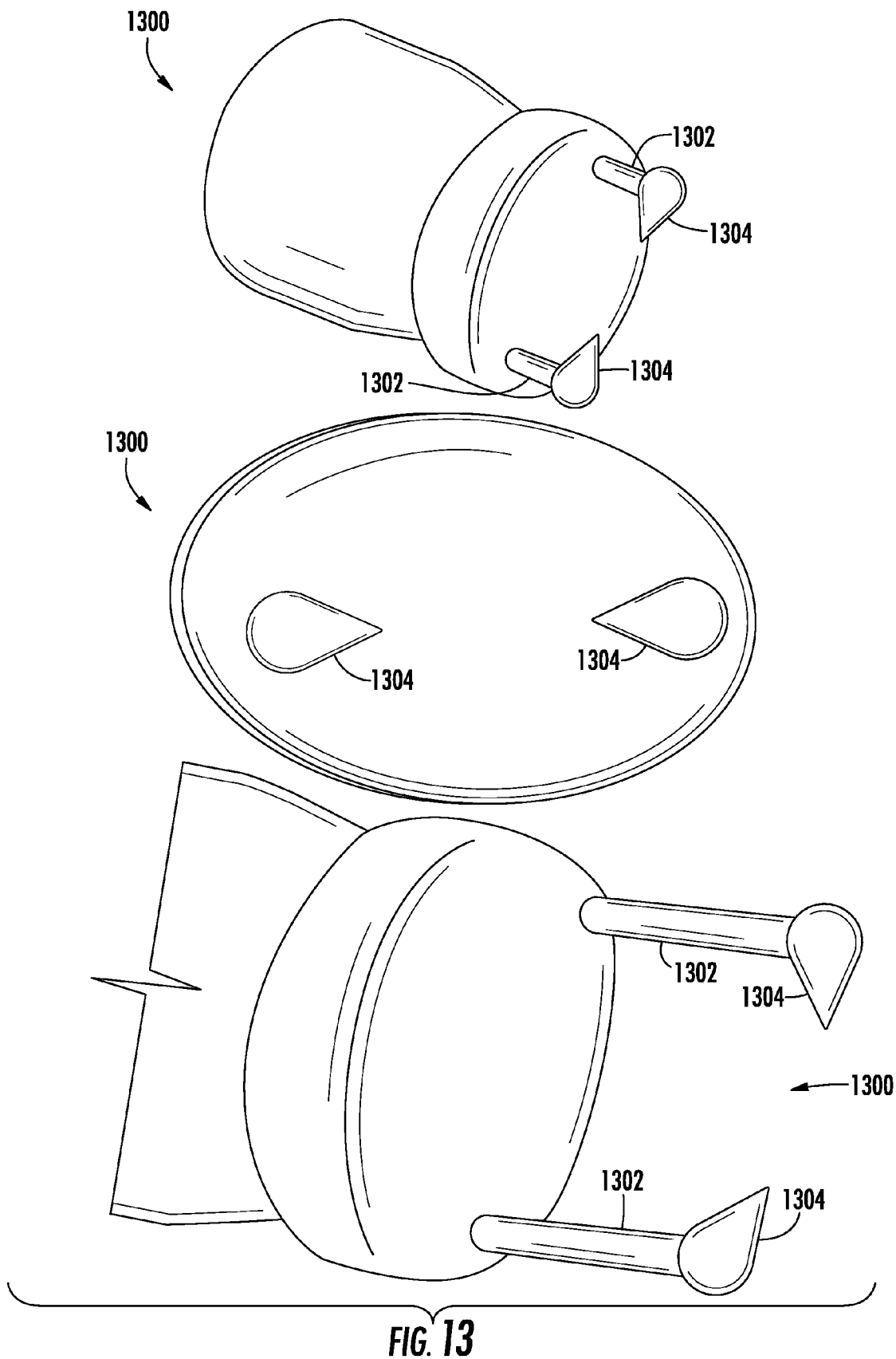
FIGS. 13, 14, 15 and 16 illustrate various handheld nerve conduction stimulators according to example implementations.
Figure 14:
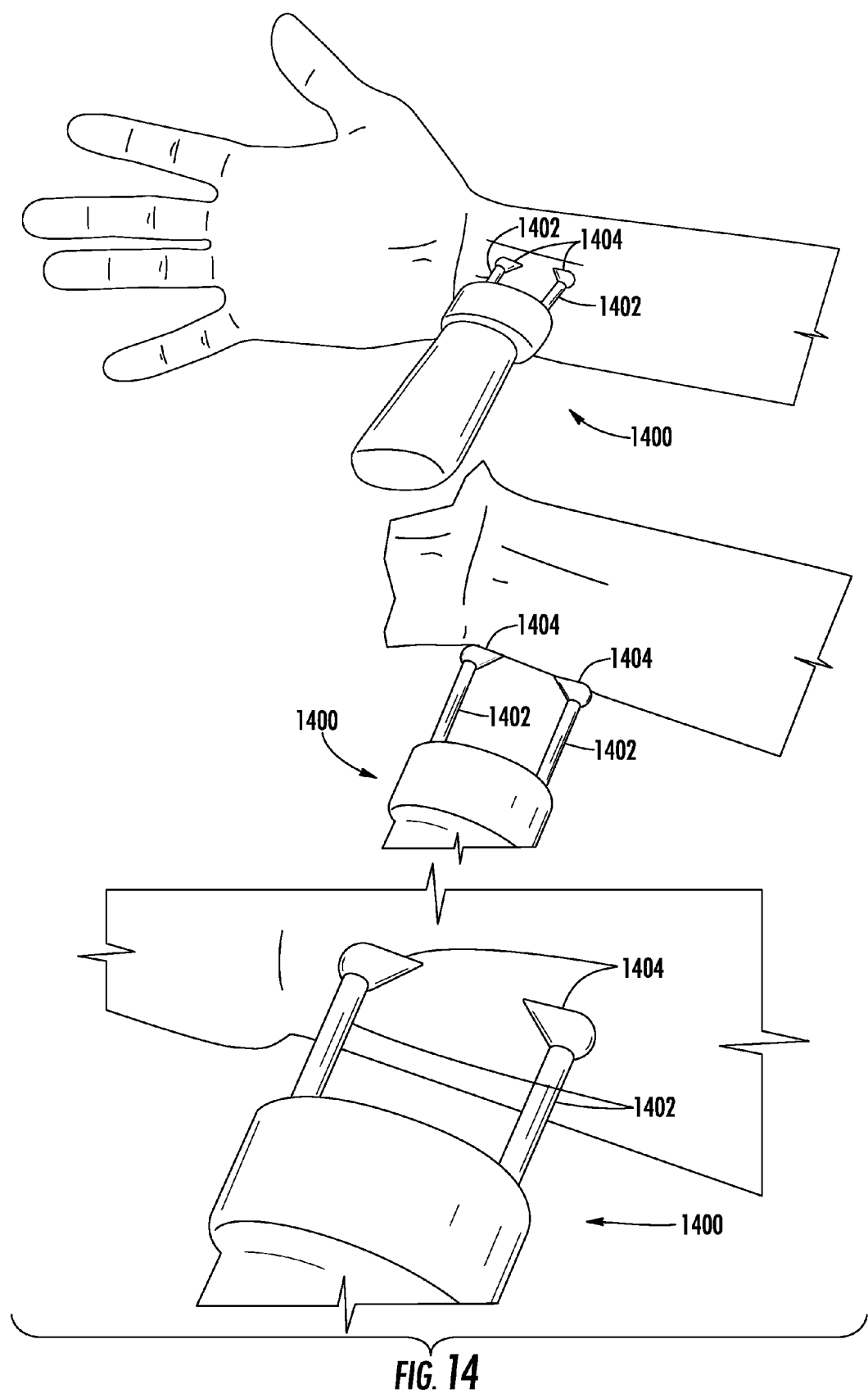
Figure 15:
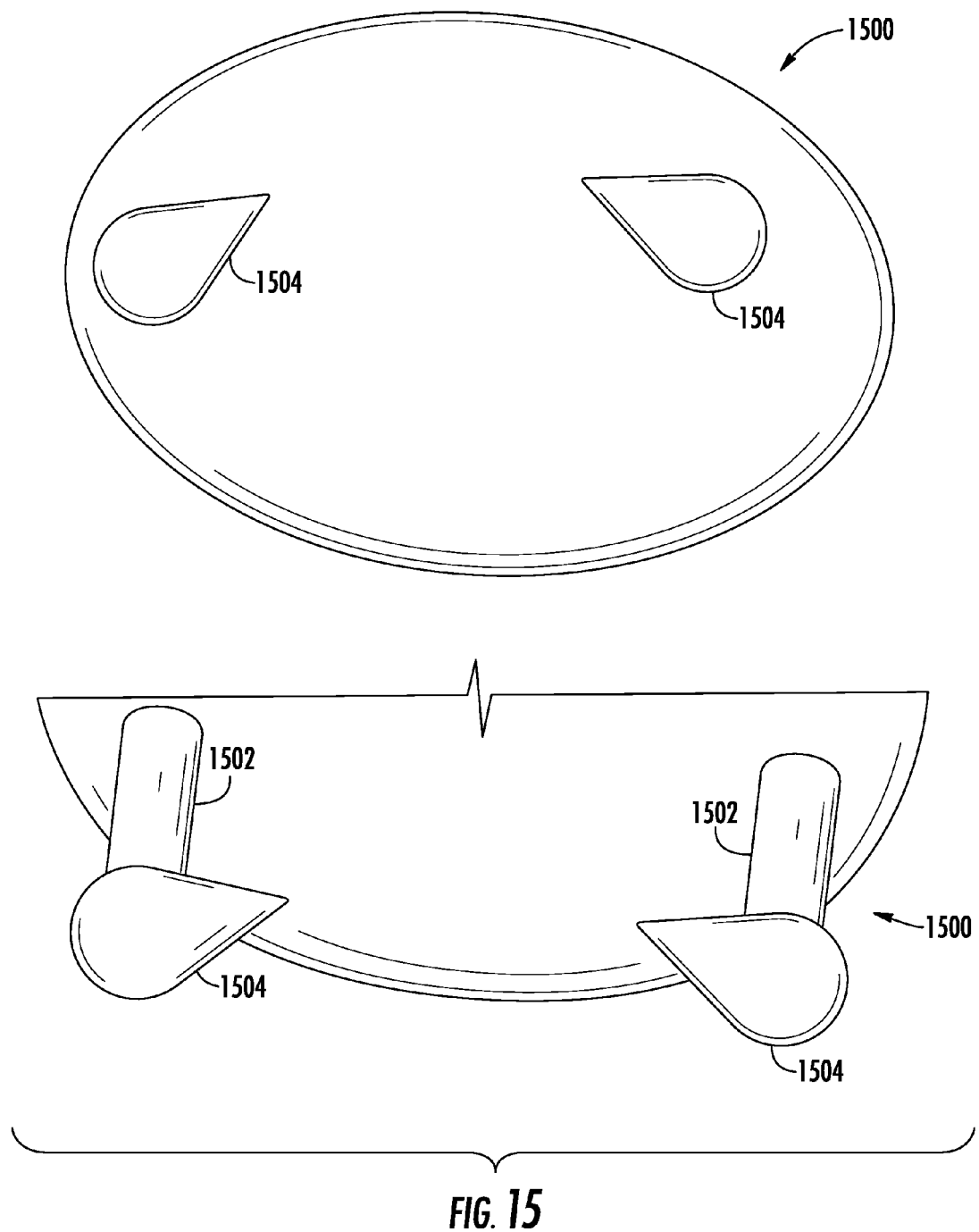
Figure 16:
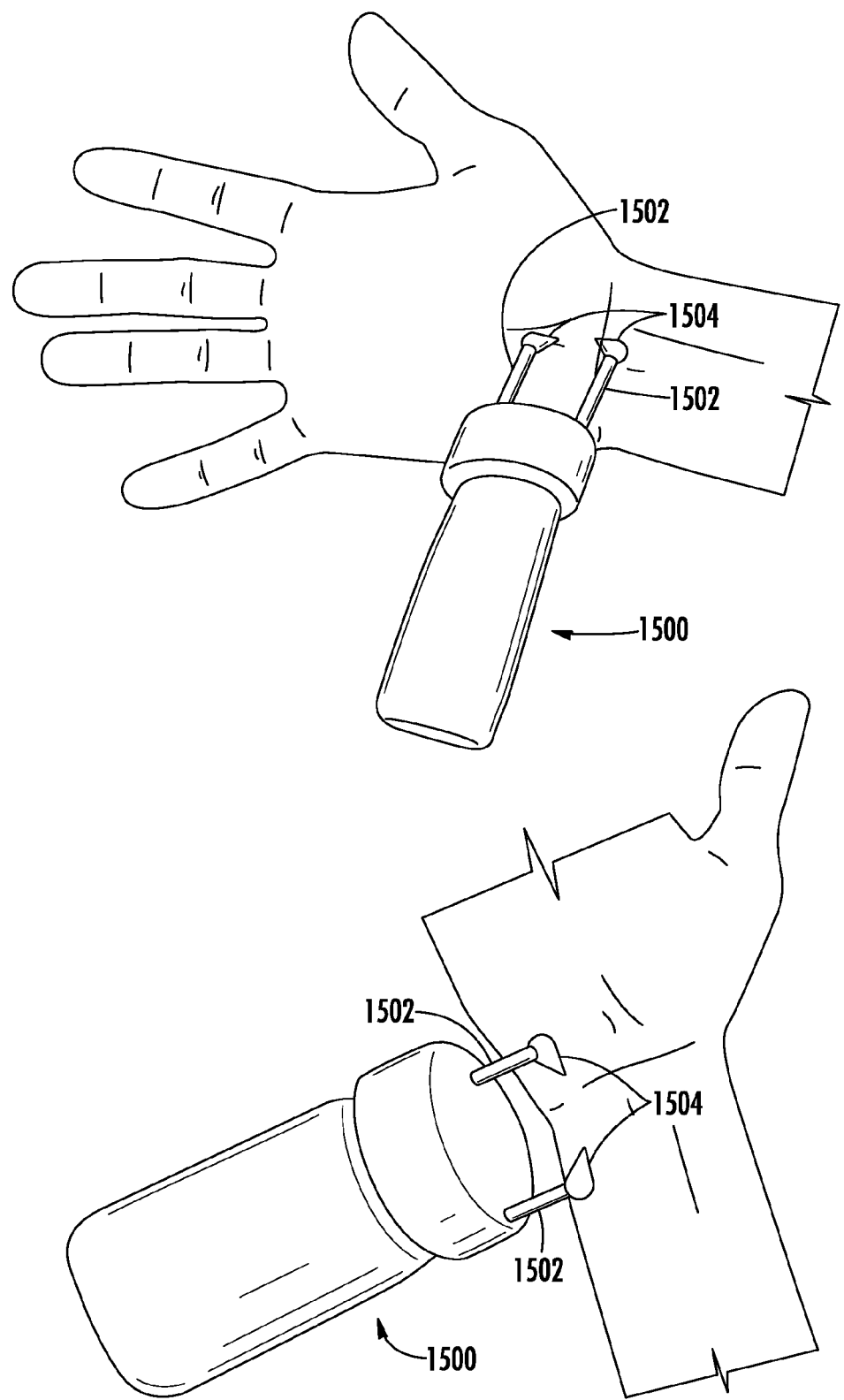

FIG. 11 illustrates the use of focal tissue stimulators 1100 with bar conductors (electrodes) 1102 including pointed features 1104, which may be used for recording as well as stimulating tissue. FIG. 12 illustrates a handheld nerve stimulator 1200 (often used in neurodiagnostic studies) that may benefit from the pointed features of example implementations. In this regard, FIG. 13 shows a handheld nerve conduction stimulator 1300 with conductors 1302 including pointed features 1304 for focal stimulation when the handheld stimulator, and FIG. 14 illustrates the handheld stimulator 1400 with conductors 1402 including pointed features 1404 for focal stimulation against tissue. Even further, if the pointed features (focal stimulator shape) are oriented slightly differently, as shown in FIG. 15 including a focal tissue stimulator 1500 with conductors 1502 including pointed features 1504, the shape may work for side application, as often performed in nerve conduction studies. And FIG. 16 illustrates examples of the use of this handheld stimulator for side application.

Here again, in various examples, the conductors 1102, 1302, 1402, 1502, their pointed features 1104, 1304, 1404, 1504 or certain parameters of the conductors or their pointed features may vary to optimize the current density of the pathway, such as in a manner similar to that described above with reference to FIGS. 7 and 8.

In other examples, the focal tissue stimulator may be used with other types of electrodes such as electroporation electrodes, TENS electrodes, tab electrodes or the like.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of any appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of any appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A focal tissue stimulator comprising a pair of concentric conductors, the pair of concentric conductors comprising:
   an inner conductor; and
   an outer conductor having an elliptical annular shape and surrounding the inner conductor, the outer conductor having a minor axis and a mutually-perpendicular, major axis, a first portion of the outer conductor proximate the minor axis being closer in proximity to the inner conductor than a second portion of the outer conductor proximate the major axis, wherein the inner conductor includes a first pair of opposing, outwardly-extending pointed features that lie on an axis of the inner conductor coincident with the minor axis of the outer conductor, wherein the outer conductor includes a second pair of facing, inwardly-extending pointed features that lie on the minor axis of the outer conductor, the pointed features of the second pair of pointed features facing respective pointed features of the first pair of pointed features to focus the current density of the pathway, and wherein the inner and outer conductors are coupled or couplable to respective leads configured to deliver current for passage therebetween, the elliptical annular shape of the outer conductor creating a pathway of increased current density at the first portion relative to the second portion.

2. The focal tissue stimulator of claim 1, wherein a distance of either or both of the minor axis or major axis is selected to optimize the current density of the pathway.

3. The focal tissue stimulator of claim 1, wherein the pointed features of the first pair of pointed features are symmetric about the axis of the inner conductor coincident with the minor axis of the outer conductor, and wherein the pointed features of the second pair of pointed features are symmetric about the minor axis of the outer conductor.

4. The focal tissue stimulator of claim 1, wherein at least one of a length or sharpness of the pointed features of either or both the first or second pair of pointed features is selected to optimize the current density of the pathway.

5. The focal tissue stimulator of claim 1, wherein the inner conductor includes a plurality of first pairs of opposing, outwardly-extending pointed features the plurality of which lie on the axis of the inner conductor coincident with the minor axis of the outer conductor, and wherein the outer conductor includes a plurality of second pairs of facing, inwardly-extending pointed features the plurality of which lie on the minor axis of the outer conductor, the pointed features of the second pairs of pointed features facing respective pointed features of the first pairs of pointed features to focus the current density of the pathway.

6. The focal tissue stimulator of claim 5, wherein a distance between adjacent pointed features of either or both the first or second pairs of pointed features is selected to optimize the current density of the pathway.

7. The focal tissue stimulator of claim 5, wherein an orientation of adjacent pointed features of either or both the first or second pairs of pointed features is selected to optimize the current density of the pathway.

8. The focal tissue stimulator of claim 5, wherein the plurality of first pairs of pointed features is symmetric about the axis of the inner conductor coincident with the minor axis of the outer conductor, and wherein the plurality of second pairs of pointed features is symmetric about the minor axis of the outer conductor.

9. A focal tissue stimulator comprising a pair of concentric conductors, the pair of concentric conductors comprising:

an inner conductor; and an outer conductor surrounding the inner conductor, the inner and outer conductors having respective coincident axes, wherein the inner conductor includes a first pair of opposing, outwardly-extending pointed features that lie on the axis of the inner conductor, and the outer conductor includes a second pair of facing, inwardly-extending pointed features that lie on the axis of the outer conductor and face respective pointed features of the first pair of pointed features, wherein the inner and outer conductors are coupled or couplable to respective leads configured to deliver current for passage therebetween, the pointed features of the inner and outer conductors creating a pathway of increased current density relative to the first and second conductors absent the pointed features.

* * * * *